United States Patent

Mueninghoff et al.

[11] Patent Number: 6,068,849
[45] Date of Patent: May 30, 2000

[54] SURFACTANTS FOR USE IN AGRICULTURAL FORMULATIONS

[75] Inventors: Jane C. Mueninghoff, West Chester; Roger H. Garst, Cincinnati, both of Ohio

[73] Assignee: Henkel Corporation, Gulph Mills, Pa.

[21] Appl. No.: 08/892,593

[22] Filed: Jul. 14, 1997

[51] Int. Cl.⁷ ....................................... A01N 25/30
[52] U.S. Cl. ............................ 424/405; 514/785; 504/116
[58] Field of Search ...................... 424/405, 407; 514/785, 919, 920; 504/116

[56] References Cited

U.S. PATENT DOCUMENTS

| | | | |
|---|---|---|---|
| 4,869,896 | 9/1989 | Coulston et al. | 424/45 |
| 5,116,401 | 5/1992 | Young | 71/86 |
| 5,356,861 | 10/1994 | Gednalski et al. | 504/206 |
| 5,559,078 | 9/1996 | Garst | 504/116 |
| 5,711,953 | 1/1998 | Bassett | 424/405 |

FOREIGN PATENT DOCUMENTS 9622109  7/1996  European Pat. Off. .

*Primary Examiner*—Neil S. Levy
*Attorney, Agent, or Firm*—Ernest G. Szoke; Wayne C. Jaeschke; Steven J. Trzaska

[57] ABSTRACT

An adjuvant containing: (a) a $C_6$–$C_{22}$ fatty acid methyl ester ethoxylate having from 1 to about 200 moles of ethylene oxide; and (b) a component selected from the group consisting of nonionic surfactants, anionic surfactants, cationic surfactants, alkyl esters, phytobland mineral oils, water soluble silicone surfactants, fatty acid dialkyl ethers, fatty acid dialkyl carbonates, vegetable oils, and mixtures thereof.

15 Claims, No Drawings

SURFACTANTS FOR USE IN AGRICULTURAL FORMULATIONS

FIELD OF THE INVENTION:

The present invention generally relates to surfactants for agricultural formulations. More particularly, the invention relates to the use of fatty acid methyl ester ethoxylates as emulsifiers, dispersants, wetting agents and solvents for adjuvant concentrates, pesticide compositions, and aqueous pesticide compositions.

BACKGROUND OF THE INVENTION

Insecticides, insect repellents, fungicides, bactericides, bacteriostats, herbicides, and plant growth regulators are normally formulated into various products for use on crops, for insect control, weed control and the like. Alternatively, the products may be formulated as liquids or powders or granules. Solvents, emulsifiers, dispersing agents and wetting agents are normally incorporated into such compositions to ensure the preparation of a uniform pesticide formulation.

These formulation components are also selected to ensure that the pesticide composition will disperse or emulsify evenly in a tank mix at the point of application. They also have a third purpose which is to ensure optimum delivery of the tank mix preparation to the targeted pest or substrate. Sometimes these surfactants incorporated in pesticide formulations are not sufficient to fully ensure stable tank mixes when such tank mixes contain multiple components. Similarly, it may be necessary to add adjuvants to the tank mix for full stability. It is widely known that adding adjuvants which contain surfactants to the tank mix will realize the desired stabilization. Moreover, additional quantities of surfactants have been shown to potentiate pesticidal activity of many pesticides and there are many adjuvant formulations that have been developed for this purpose. Surfactants are nearly always components of these adjuvants ranging from minor components to the sole component.

Fatty acid methyl ester ethoxylates are a class of nonionic surfactants which enjoy the advantage that they can be prepared from renewable resources, such as natural fats and oils. The fatty acid methyl ester ethoxylates are readily biodegradable and exhibit very low aquatic toxicity. These features commend fatty acid methyl ester ethoxylates to formulators of pesticides and adjuvants seeking to prepare formulations of products with minimum levels of environmental impact and safe handling properties.

SUMMARY OF THE INVENTION:

The present invention is directed to an adjuvant containing:

(a) an ethoxylated fatty acid methyl ester corresponding to formula I:

$$R_1\text{—CO(OCH}_2\text{CH}_2)_n\text{—OCH}_3 \qquad (I)$$

wherein $R_1$ is a saturated or unsaturated alkyl group containing from about 6 to about 22 carbon atoms and n is an integer from 1 to about 200; and (b) a component selected from the group consisting of nonionic surfactants, anionic surfactants, cationic surfactants, alkyl esters, phytobland mineral oils, water soluble silicone surfactants, fatty dialkyl ethers, fatty dialkyl carbonates, vegetable oils, and mixtures thereof.

The present invention is also directed to a pesticide concentrate containing:

(a) a fatty acid methyl ester ethoxylate; and (b) a biologically-active ingredient.

The present invention is also directed to an aqueous pesticide composition containing:

(a) a fatty acid methyl ester ethoxylate;

(b) a biologically-active ingredient; and (c) water.

The present invention is also directed to a process for treating a target substrate involving contacting the target substrate with the above-disclosed aqueous pesticide composition.

DESCRIPTION OF THE INVENTION

Other than in the claims and in the operating examples, or where otherwise indicated, all numbers expressing quantities of ingredients or reaction conditions used herein are to be understood as being modified in all instances by the term "about".

The term target substrate as used herein means a plant, a plant pest, or a combination of a plant and a plant pest. A plant pest is defined as any living stage of any weed, insects, mites, nematodes, slugs, snails, protozoa, or other invertebrate animals, bacteria, fungi, other parasitic plants or reproductive parts thereof, viruses, or any organisms similar to or allied with any of the foregoing, or any infectious substances which can directly or indirectly injure or cause disease or damage in any plants or parts thereof, or any processed, manufactured, or other products of plants.

The fatty acid methyl ester ethoxylate of the present invention can provide a variety of functions in agricultural applications. These functions include: (1) solubilizing biologically-active ingredients combined therewith; (2) acting as a co-solvent when combined with other organic materials used in the formulation of adjuvant and pesticide concentrates; (3) act as an emulsifier for a biologically active ingredient when diluted with water; and (4) facilitate the enhanced application of an aqueous, ready-to-use pesticide composition when it is applied onto a target substrate. Suitable fatty acid methyl ester ethoxylates include those of formula I:

$$R_1\text{—CO(OCH}_2\text{CH}_2)_n\text{—OCH}_3 \qquad (I)$$

wherein $R_1$ is a saturated or unsaturated alkyl group containing from about 6 to about 22 carbon atoms, and preferably from about 10 to about 18 carbon atoms, and n is an integer from 1 to about 200, preferably from about 3 to about 100, and most preferably from about 5 to about 30.

The reason that the fatty acid methyl ester ethoxylates of formula I are capable of facilitating the above-disclosed functions is that because fatty acid methyl esters are oil soluble, they allow for the formulation of an adjuvant and/or pesticide concentrate containing various organic liquids such as, for example, co-surfactants which include nonionic, anionic, cationic and amphoteric surfactants, as well adjuvants based on both synthetic and vegetable oils. Once the methyl esters are ethoxylated, the ethylene oxide substituents render the methyl ester more water soluble. Hence, when a pesticide concentrate containing both a solvated biologically active ingredient and an ethoxylated methyl ester is diluted with water to form a ready-to-use aqueous pesticide composition, the biologically active ingredient is successfully emulsified into droplets which when applied onto a target substrate, enables the biologically active ingredient to spread across the substrate by the mechanism of surface chemistry.

While a pesticide concentrate may be successfully formulated using only an ethoxylated methyl ester as a solvent/surfactant, it is oftentimes desirable to combine the methyl ester ethoxylate with a co-surfactant/solvent, in order to provide added solubilizing, emulsifying, dispersing and wetting properties. Examples of suitable co-surfactants/solvents include, for example, other nonionic surfactants such as ethoxylated castor oils, alcohol ethoxylates, alkyl polyglycosides, glucamides and the like, anionic surfactants such as fatty alcohol ether sulfates, phosphate esters, sulfonates, and the like, cationic surfactants such as ethoxylated fatty amines, and the like, alkyl esters such as methyl oleate, ethyl canolate, and methyl soyate, phytobland mineral oils, water-soluble silicone surfactants, fatty dialkyl ethers, fatty dialkyl carbonates, vegetable oils such as canola oil, soybean oil and the like, and mixtures thereof, typically employed in adjuvant and pesticide compositions.

The co-surfactant/solvent of the present invention will typically be present in the composition in an amount of from about 1 to about 99% by weight, preferably from about 10 to about 95% by weight, and most preferably from about 25 to about 90% by weight, based on the weight of the adjuvant.

According to another embodiment of the present invention, there is provided a pesticide concentrate containing a mixture of the above-disclosed adjuvant and a biologically active ingredient.

Suitable biologically-active ingredients for use in the pesticide concentrates of the present invention are generally selected from the group consisting of insecticides, insect repellents, fungicides, bactericides, bacteriostats, herbicides, and plant growth regulators, all of which are based on biologically-active ingredients. Suitable insecticides include, for example,
O,O-diethyl
  O-(2-isopropyl-4-methyl-6-pyrimidinyl)phosphorothioate,
O,O-diethyl S-2-[(ethylthio)ethyl]phosphorodithioate,
O,O-dimethyl O-(3-methyl-4-nitrophenyl)thiophosphate,
O,O-dimethyl
  S-(N-methylcarbamoylmethyl)phosphorodithioate,
O,O-dimethyl S-(N-methyl-N-formylcarbamoylmethyl) phosphorodithioate, O,O-dimethyl
S-2-[(ethylthio)ethyl]phosphorodithioate, O,O-diethyl S-2-[(ethylthio)ethyl]phosphorodithioate,
O,O-dimethyl-1-hydroxy-2,2,2-trichloroethylphosphonate,
O,O-diethyl-O-(5-phenyl-3-isooxazolyl)phosphorothioate,
O,O-dimethyl
  O-(2,5-dichloro-4-bromophenyl)phosphorothioate,
O,O-dimethyl-O-)3-methyl-4-methylmercaptophenyl) thiophosphate, O-ethyl
O-p-cyanophenyl-O-phenylphosphorothioate,
O,O-dimethyl-S-(1,2-dicarboethoxyethyl) phosphorodithioate,
2-chloro-(2,4,5-trichlorophenyl)vinyldimethyl phosphate,
2-chloro-1-(2,4-dichlorophenyl)vinyldimethyl phosphate,
O,O-dimethyl O-p-cyanophenyl phosphorothioate,
2,2-dichlorovinyl dimethyl phosphate, 0,0-diethyl
O-2,4-dichlorophenyl phosphorothioate, ethyl mercaptophenylacetate O,O-dimethyl phosphorodithioate,
S-[(6-chloro-2-oxo-3-benzooxazolinyl)methyl]O,O-diethyl phosphorodithioate, 2-chloro-1-(2,4-dichlorophenyl) vinyl diethylphosphate O,O-diethyl
O-(3-oxo-2-phenyl-2H-pyridazine-6-yl)phosphorothioate,
O,O-dimethyl S-(1-methyl-2-ethylsulfinyl)-ethyl phosphorothiolate, O,O-dimethyl S-phthalimidomethyl phosphorodithioate, O,O-diethyl 2,2,2-trichloroethanol,
2-(p-tert-butyl-phenoxy)isopropyl-2'-chloroethylsulfite, azoxybenzene, di-(p-chlorophenyl)-cyclopropyl carbinol, di[tri(2,2-dimethyl-2-phenylethyl)tin]oxide,
1-(4-chlorophenyl)-3-(2,6-difluorobenzoyl)urea and S-tricyclohexyltin O,O-diisopropylphosphorodithioate; 2-methyl-2-(methylthio)propionaldehyde O-(methylcarbamoyl)oxime; ethyl [2-(4-phenoxyphenoxy)ethyl] carbamate;
butyl-2,3-dihydro-2,2-dimethylbenzofuran-7-yl N,N'-dimethyl-N,N'-thiodicarbamate; 1-naphthyl methyl carbamate; 2-(ethylthiomethyl)phenyl methylcarbamate; 5-(4-phenoxybutyl)dimethylthiocarbamate;
dimethyl N,N'-(thiobis(methylimino)carbonyloxy)-bis (ethanimidothioate); (RS)-α-cyano-3-phenoxybenzyl-(RS)-2-(4-chlorophenyl)-3-methylbutyrate; (RS)-α-cyano-3-phenoxyphenyl-(RS)-2,2-dichloro-1-(4-ethoxyphenyl)cyclopropanecarboxylate; (RS)-α-cyano-3-phenoxybenzyl-N-(2-chloro-α,α,α-trifluoro-p-tolyl-D-valinate;
3-phenoxybenzyl-(1RS)-cis,trans-3-(2,2-dichlorovinyl)-2, 2-dimethylcyclopropanedicarboxylate.

Insect repellents which may be employed include but are not limited to 2-ethyl-1,3-hexanediol; N-octyl bicycloheptene dicarboximide; N,N-diethyl-M-toluamide; 2,3:4,5-Bis (2-butylene) tetrahydro-2-furaldehyde; Di-n-propyl isocinchomeronate; and 2-hydroxyethyl-n-octyl sulfide.

Fungicides which may be employed include but are not limited to 3,3'-ethylenebis (tetrahydro-4,6-dimethyl-2H-1,3, 5-thiadiazine-2-thione), zinc or manganese ethylenebis (dithiocarbamate), bis-(dimethyldithiocarbamoyl)disulfide, zinc propylenebis (dithiocarbamate), bis (dimethyldithiocarbamoyl) ethylenediamine; nickel dimethyldithiocarbamate, methyl-1(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate and 5-methyl-10-butoxycarbonylamino-10, 11-dehydrodibenzo (b,f)azepine; pyridine fungicides such as zinc bis(1-hydroxy-2(1H) pyridinethionate and
2-pyridinethiol-1-oxide sodium salt; O,O-diisopropyl S-benzylphosphorothioate and O-ethyl S,S-diphenyldithiophosphate; phthalimide fungicides such as N-(2,6-p-diethylphenyl)phthalimide and
N-(2,6-diethylphenyl)-4-methylphthalimide; dicarboxyimide fungicides such as N-trichloromethylthio 4-cyclohexene-1,2-dicarboxyimide and
N-tetrachloroethylthio-4-cyclohexene-1,2-dicarboxyimide; 5,6-dihydro-2-methyl-1,4-oxathine-3-carboxanilido-4,4-dioxide and 5,6-dihydro-2-methyl-1, 4-oxathine-3-carboxanilide; naphthoquinone fungicides such as 2,3-dichloro-1,4-naphthoquinone, 2-oxy-3-chloro-1,4-naphthoquinone copper sulfate, pentachloronitrobenzene;
1,4-dichloro-2,5-dimethoxybenzene;
5-methyl-s-triazol-(3,4-b)benzthiazole;
2-(thiocyanomethylthio)benzothiazole;
3-hydroxy-5-methylisooxazole;
N-2,3-dichlorophenyltetrachlorophthalamic acid;
5-ethoxy-3-trichloromethyl-1,2,4-thiazidazole;
2,4-dichloro-6-(0-chloroanilino)-1,3,5-triazine;
2,3-dicyano-1,4-dithioanthraquinone; copper 8-quinolinate; polyoxine; validamycin; cycloheximide; iron methanearsonate; diisopropyl 1,3-dithiolane-2-iridene malonate;
3-allyloxy-1,2-benzoisothiazol-1,1-dioxide;
kasugamycin; Blasticidin S; 4,5,6,7-tetrachlorophthalide;
3-(3,5-dichlorophenyl)5-ethenyl 5-methyloxazolizine-2,4-dione;

N-(3,5-dichlorophenyl)-1,2-dimethylcyclopropane-1,2-dicarboxyimide; S-n-butyl-5'-para-t-butylbenzyl-N-3-pyridyldithiocarbonylimidate;
4-chlorophenoxy-3,3-dimethyl-1-(1H,1,3,4-triazol-1-yl)-2-butanone;
methyl-D,L-N-(2,6-dimethylphenyl)-N-(2'-methoxyacetyl)alaninate;
N-propyl-N-[2-(2,4,6-trichlorophenoxy)ethyl]imidazol-1-carboxamide; N-(3,5-dichlorophenyl)succinamide; tetrachloroisophthalonitrile;
2-dimethylamino-4-methyl-5-n-butyl-6-hydroxypyrimidine;
2,6-dichloro-4-nitroaniline;
3-methyl-4-chlorobenzthiazol-2-one;
1,2,5,6-tetrahydro-4H-pyrrolol-[3,2,1-i,j]quinoline-2-one;
3'-isopropoxy-2-methylbenzanilide;
1-[2-(2,4-dichlorophenyl)-4-ethyl-1,3-dioxorane-2-ylmethyl]-1H,1,2,4-triazol;
1,2-benzisothiazoline-3-one; basic copper chloride; basic copper sulfate;
N'-dichlorofluoromethylthio-N,N-dimethyl-N-phenyl sulfamide; ethyl-N-(3-dimethylaminopropyl)thiocarbamate hydrochloride; piomycin;
S,S-6-methylquinoxaline-2,3-di-yldithiocarbonate; complex of zinc and manneb; di-zinc bis(dimethyldithiocarbamate) ethylenebis (dithiocarbamate).

Plant growth regulators which may be employed include but are not limited to
N-methoxycaronyl-N'-4-methylphenylcarbamoylethylisourea and 1-(4-chlorophenylcarbamoyl)-3-ethoxycarbonyl-2-methylisourea; another type of plant growth regulators such as sodium naphthaleneacetate,
1,2-dihydropyridazine-3,6-dione and gibberellins; triazine herbicides such as
2-methylthio-4,6-bisethylamino-1,3,5-triazine,
2-chloro-4,6-bisethylamino-1,3,5-triazine,
2-methoxy-4-ethylamino-6-isopropylamino-1,3,5-triazine,
2-chloro-4-ethylamino-6-isopropylamino-s-triazine,
2-methylthio-4,6-bis(isopropylamino)-S-triazine and
2-methylthio-4-ethylamino-6-isopropylamino-s-triazine;
phenoxy herbicides such as 2,4-dichlorophenoxyacetic acid and methyl, ethyl, and butyl esters thereof.
2-chloro-4-methylphenoxyacetic acid,
4-chloro-2-methylphenoxyacetic acid and ethyl 2-methyl-4-chlorophenoxybutylate; diphenylether herbicides such as
2,4,6-trichlorophenyl-4'-nitrophenylether, 2,4-dichlorophenyl-4'-nitrophenylether and
3,5-dimethylphenyl-4'-nitrophenylether; urea herbicides such as 3-(3,4-dichlorophenyl)-1-methoxy-1-methyl urea,
3-(3,4-dichlorophenyl)-1,1-dimethylurea and
3-(4-chlorophenyl)-1,1-dimethyl urea; carbamate herbicides such as
3-methoxycarbonylaminophenyl-N-(3-methylphenyl)carbamate, isopropyl-N-(3-chlorophenyl)carbamate and methyl-N-(3,4'-dichlorophenyl)carbamate; uracil herbicides such as 5-bromo-3-sec-butyl-6-methyluracil and 1-cyclohexyl-3,5-propyleneuracil; thiolcarbamate herbicides such as
S-(4-chlorobenzyl)-N,N-diethylthiolcarbamate, S-ethyl-N-cyclohexyl-N-ethylthiolcarbamate and
S-ethyl-hexahydro-1H-azepine-1-carbothioate and
S-ethyl-N,N-di-n-propyl-thiocarbamate; pyridinium herbicides such as 1,1'-di-methyl-4,4'-bispyridinium dichloride; phosphoric herbicides such as
N-(phosphonomethyl)glycine; aniline herbicides such as alpha, alpha,
alpha-trifluoro-2,6-dinitro-N,N-dipropyl-p-toluidine,
4-(methylsulfonyl)-2,6-dinitro-N,N-dipropylaniline and N[3], N[3]-diethyl-2,4-dinitro-6 trifluoromethyl-1,3-phenylene diamine; acid anilide
herbicides such as
2-chloro-2',6'-diethyl-N-(butoxymethyl)acetanilide,
2-chloro-2',6'-diethyl-N-(methoxymethyl)acetanilide, and
3,4-dichloropropionanilide; pyrazole herbicides such as
1,3-dimethyl-4-(2,4-dichlorobenzoyl)-5-hydroxypyrazole and 1,3-di-methyl-4-(2,4-dichlorobenzoyl)-5-(p-toluenesulfonyloxy)pyrazole;
5-tert-butyl-3-(2,4-dichloro-5-isopropoxyphenyl)-1,3,4-oxadiazoline-2-one;
2-[N-isopropyl,N-(4-chlorophenyl)carbamoyl]-4-chloro-5-methyl-4-isooxazoline-3-one;
3-isopropylbenzo-2-thia-1,3-diazinone-(4)-2,4-dioxide and
3-(2-methyl-phenoxy)pyridazine.

The biologically-active ingredients of the present invention can be present in the concentrate in an amount of from about 0.1 to about 95% by weight, and preferably from about 5 to about 85% by weight, and most preferably from about 10 to about 80% by weight, based on the weight of the concentrate.

According to another embodiment of the present invention, there is thus provided a pesticide concentrate containing: (a) from about 99.9 to about 5% by weight, preferably from about 95 to about 15% by weight, and most preferably from about 90 to about 20% by weight, of a the above-disclosed adjuvant; and (b) from about 0.1 to about 95% by weight, preferably from about 5 to about 85% by weight, and most preferably from about 10 to about 80% by weight, of a biologically active ingredient.

The precise amount of biologically active ingredient contained in the pesticide concentrate will oftentimes depend upon the specific end-use application, i.e., the target substrate to be treated, the area to be treated, etc. Thus, it is within the skill of the applicator to determine the specific amount of biologically active ingredient to be used for a particular application.

According to another embodiment of the present invention, there is also provided an aqueous pesticide composition containing from about 0.1% to about 10% by weight, and preferably from about 0.5 to about 5% by weight, based on the weight of the composition, of the above-disclosed pesticide concentrate.

The precise amount of dilution of the pesticide concentrate necessary to form a ready-to-use aqueous pesticide composition will again depend upon the specific application itself, i.e., the target substrate to be treated, the area to be treated, etc. Thus, it is once again within the skill of the applicator to determine the specific amount of water needed to dilute the pesticide concentrate.

Finally, the present invention also provides a process for treating a target substrate involving contacting the target substrate with the above-disclosed aqueous pesticide composition.

The present invention will be better understood from the examples which follow, all of which are meant to be illustrative only, and are not intended to unduly limit the scope of the invention in any way.

EXAMPLES

| Component | %/wt. |
|---|---|
| Examples of Adjuvant Formulations: | |
| Example 1 | |
| $C_{18}$ methyl ester w/13 EO units | 10% |
| methyl oleate | 89% |
| water | 1% |
| Example 2 | |
| $C_{18}$ methyl ester w/13 EO units | 8% |
| methyl soyate | 88% |
| AGRIMUL ® PG 2065(*) | 4% |
| Example 3 | |
| $C_{6-10}$ methyl ester w/3 EO units | 6% |
| mineral oil | 92% |
| POE (4) lauryl alcohol | 2% |
| Examples of Pesticide Concentrates: | |
| Example 1: | |
| $C_{18}$ methyl ester w/13 EO units | 13% |
| methyl laurate | 42.5% |
| Chloropyrifos | 42.5% |
| calcium dodecylbenzene sulfonate | 2% |
| Example 2: | |
| $C_{18}$ methyl ester w/13 EO units | 4% |
| methyl canolate | 82% |
| AGRIMUL ® PG 2065 | 2% |
| calcium dodecylbenzene sulfonate | 2% |
| 2,4 D octyl ester | 10% |

(*)AGRIMUL ® PG 2065 Surfactant-an alkyl polyglycoside in which the alkyl group contains 8 to 10 carbon atoms and has an average degree of polymerization of 1.7.

What is claimed is:

1. A pesticide concentrate comprising:
   (a) an adjuvant containing:
      (i) from about 1 to about 99% by weight of an ethoxylated fatty acid methyl ester corresponding to formula I:

$$R_1-CO(OCH_2CH_2)_n-OCH_3 \qquad (I)$$

wherein $R_1$ is a saturated or unsaturated alkyl group containing from about 6 to about 22 carbon atoms, n is an integer from 1 to about 200; and
      (ii) from about 1 to about 99% by weight of a component selected from the group consisting of nonionic surfactants, anionic surfactants, cationic surfactants, alkyl esters, phytobland mineral oils, water soluble silicone surfactants, fatty acid dialkyl ethers, fatty acid dialkyl carbonates, vegetable oils, and mixtures thereof; and
   (b) from about 0.1 to about 95% by weight of a biologically active ingredient selected from the group consisting of insecticides, insect repellents, fungicides, bactericides, bacteriostats, herbicides, plant growth regulators, and mixtures thereof.

2. The concentrate of claim 1 wherein the component is an alkyl ester.

3. The concentrate of claim 1 wherein the component is a fatty acid dialkyl carbonate.

4. The concentrate of claim 1 wherein the component is a vegetable oil.

5. The concentrate of claim 1 wherein the component is a phytobland mineral oil.

6. The concentrate of claim 1 wherein the component is a nonionic surfactant.

7. The concentrate of claim 6 wherein the nonionic surfactant is an alkyl polyglycoside.

8. The concentrate of claim 1 wherein the component is an anionic surfactant.

9. The concentrate of claim 1 wherein the component is a cationic surfactant.

10. The concentrate of claim 1 wherein the component is a water soluble silicone surfactant.

11. The concentrate of claim 1 wherein the biologically active ingredient is present in an amount of from about 5 to about 85% by weight, based on the weight of the concentrate.

12. A pesticide concentrate comprising:
   (a) from about 90 to about 20% by weight of an adjuvant, the adjuvant containing:
      (i) from about 10 to about 75% by weight of an ethoxylated fatty acid methyl ester corresponding to formula I:

$$R_1-CO(OCH_2CH_2)_n-OCH_3 \qquad (I)$$

wherein $R_1$ is a saturated or unsaturated alkyl group containing from about 10 to about 18 carbon atoms, n is an integer from about 5 to about 30; and
      (ii) from about 90 to about 25% by weight of a nonionic co-surfactant, the weights of (i) and (ii) being based on the weight of the adjuvant; and
   (b) from about 10 to about 80% by weight of a biologically active ingredient selected from the group consisting of insecticides, insect repellents, fungicides, bactericides, bacteriostats, herbicides, plant growth regulators, and mixtures thereof, the weights of (a) and (b) being based on the weight of the concentrate.

13. An aqueous pesticide composition comprising:
   (a) from about 0.1 to about 10% by weight of the pesticide concentrate of claim 1.

14. A process for treating a target substrate comprising contacting the substrate with the aqueous pesticide composition of claim 13.

15. The process of claim 14 wherein the target substrate is selected from the group consisting of a plant, a plant pest, and a combination of a plant and a plant pest.

* * * * *